United States Patent [19]

Queen et al.

[11] Patent Number: 5,503,847
[45] Date of Patent: Apr. 2, 1996

[54] HYDROCOLLOID WOUND GEL

[75] Inventors: Douglas Queen, Wirral; Lesley A. Chambers, Flint; Simon M. Adams, Chester; Hugh Delargy, Merseyside, all of United Kingdom

[73] Assignee: E. R. Squibb and Sons, Inc., Princeton, N.J.

[21] Appl. No.: 47,319

[22] Filed: Apr. 15, 1993

[51] Int. Cl.$^6$ .............................. A61K 9/10; A61K 47/36; A61K 47/40

[52] U.S. Cl. .................. 424/488; 252/315.3; 252/315.4; 514/944

[58] Field of Search ...................................... 424/484–485, 424/488; 524/916; 252/315.3, 315.4; 514/944

[56] References Cited

U.S. PATENT DOCUMENTS

| | | | |
|---|---|---|---|
| 3,640,741 | 2/1972 | Etes | 424/401 |
| 4,140,807 | 2/1979 | Braverman | 426/573 |
| 4,813,942 | 3/1989 | Alvarez | 424/445 |

Primary Examiner—Edward J. Webman
Attorney, Agent, or Firm—Theodore R. Furman, Jr.

[57] ABSTRACT

A hydrocolloid wound gel composition useful for cleansing an debriding wounds and having some capacity for absorbing wound exudate and a method of treating wounds comprising applying the hydrocolloid wound gel to a wound.

The composition includes sodium carboxymethylcellulose, pectin, propylene glycol and water.

6 Claims, No Drawings

HYDROCOLLOID WOUND GEL

BACKGROUND OF THE INVENTION

1. Field of the Invention

This invention relates to a hydrocolloid wound gel. More particularly, this invention relates to a hydrocolloid wound gel useful for cleansing and debriding wounds and having some moisture absorption capacity.

The invention also relates to a method of treating a wound comprising applying the wound gel to a wound. It is particularly useful for the filling of cavity wounds.

2. Description of the Prior Art

It is well known that the cleansing and debriding of wounds and the removal of wound exudates is important to the process of healing of wounds. Commonly used wound dressings utilize gauze, foams, sponges, cotton wads or other fibrous materials. Gauze and other fibrous materials absorb fluids by capillary action. However, gauze and other fibrous materials have the disadvantage in that when new tissue is formed, in the process of healing, it engulfs the fibers of these materials and it is torn when the material is removed causing wound injury on removal.

Various other materials have been used, such as gels, hydrogels, granules and pastes to remove exudates from wounds. Scherisorb Gel marketed by Smith & Nephew containing propylene glycol and a starch-acrylamide t-graft co-polymer has been used as an interactive wound treatment.

SUMMARY OF THE INVENTION

The present invention provides a hydrocolloid wound gel composition which cleanses and debrides wounds and has some exudate absorption capacity. The wound gel promotes healing of wounds. The hydrocolloid wound gel contains from about 0.05% to 1.0% by weight of pectin, from about 2.0% to 4.5% sodium carboxymethylcellulose, from about 15.0% to 20.0% by weight of propylene glycol and the remainder water to make 100% by weight.

The invention is also directed to a method of wound healing which comprises placing the hydrocolloid wound gel into the wound to cleanse, debride the wound and absorb exudate to promote wound healing.

The hydrocolloid wound gel keeps the wound bed moist and produces a wound environment suitable for healing. The gel cleanses the wound, debrides necrotic matter from the wound, absorbs exudate without dessiccating or dehydrating the wound bed and promotes wound healing. Freshly generated tissue does not grow into the gel causing injury on removal. The hydrocolloid wound gel of this invention is particularly useful for chronic cavity type wounds and for wounds containing sloughy or necrotic material.

Detailed Description of the Invention

The hydrocolloid wound gel composition of the present invention contains from about 0.05% to 1.0% by weight of pectin, from about 2.0% to 4.5% by weight of sodium carboxymethylcellulose, from about 15.0% to 20.0% by weight of propylene glycol and the remainder water to make 100%.

The most preferred hydrocolloid wound gel contains 0.1% pectin, 3.4% sodium carboxymethylcellulose, 15% propylene glycol and 81.5% water.

The pectin is present in the gel composition in an amount of 0.05% to 1.0% by weight and preferably 0.1%. The preferred pectin is a high ester pectin derived from citrus peel consisting chiefly of the partial methyl esters of polygalacturonic acid (approximately 65% of the carboxyl groups are esterfied). Representative of the pectin useful in the gel composition is that marketed under the name GENU pectin type VIS-L by Copenhagen Pectin.

The gel composition contains sodium carboxymethylcellulose in the amount of 2.0% to 4.5% by weight and preferably 3.4%. The preferred sodium carboxymethylcellulose is a high viscosity sodium carboxymethylcellulose (typically in the range 2000– 4500 CPS as measured by Brookefield LV Viscometry of a 1% solution, oven dry basis, 25° C. (spindle 4/30 rpm).

Propylene glycol is present in the amount of 15.0% to 20.0% by weight and preferably 15%.

The water used in the present invention is preferably purified and pyrogen free water and is present in an amount sufficient to bring the composition up to 100% weight and in the preferred composition constitutes 81.5% by weight.

Various optional ingredients can also be included in the final composition such as preservatives, e.g., methylhydroxybenzoate and propylhydroxybenzoate. In addition, the hydrocolloid wound gel composition can, if desired, contain small amounts (effective amount), i.e., less than 5%, of pharmacologically active ingredients. For example, an antibiotic or antimicrobial agent such as metronidazole, silver sulfadiazine, neomycin or penicillin, an antiseptic agent such as povidone iodine, an anti-inflammatory agent such as hydrocortisone or triamcinoloone acetonide, or a skin protective agent such as zinc oxide can be included in the composition.

The hydrocolloid wound gel of this invention is prepared by mixing pectin in water with heating (for example at a temperature from about 50° to 60° C.) to form a solution. Propylene glycol is added while mixing and sodium carboxymethylcellulose gradually added with constant mixing to form the gel.

The composition may be packaged in conventional containers, for example, squeeze tube containers or jars and sterilized by wet heat.

The following examples are intended to illustrate the invention described herein without unduly restricting it.

EXAMPLE 1

A gel composition was prepared having the following composition:

|  | % by Weight | Weight |
| --- | --- | --- |
| Pectin | 0.1% | 0.2 g |
| Sodium Carboxymethyl-cellulose | 3.4% | 6.8 g |
| Propylene glycol | 15.0% | 30.0 g |
| Purified Water | 81.5% | 163.0 g |

Pectin (0.2 g) was added to purified water (163.0 g) in a beaker heated to 50°–60° C. with constant stirring until the pectin was dissolved. Propylene glycol (30.0 g) was added and sodium carboxymethylcellulose (6.8 g) was gradually added with constant mixing. A hydrocolloid gel (200 g) was produced.

The gel was packaged in epoxy lined aluminum tubes sealed and terminally sterilized by wet heat at 121° C. for 30 minutes. The gel when applied to a wound or body surface has good cohesive properties and remains in situ.

EXAMPLES 2–3

Following the procedure described in Example 1, and using the following compositions:

|  | Example 2 % by Weight | Example 3 % by Weight |
|---|---|---|
| Pectin | 0.7% | 0.9% |
| Sodium Carboxymethyl-cellulose | 4.0% | 2.5% |
| Propylene glycol | 20.0% | 17.0% |
| Purified Water | 75.3% | 79.6% |

The hydrocolloid wound gel of the present invention cleanses and debrides wounds and absorbs large quantities of wound exudate. The gel enhances wound healing. The main application of the gel is directed to chronic necrotic or sloughy wounds, with large cavities, where debridement absorption and filling are indicated. The wound gel is also useful in treatment of ulcers, burns, pressure sores, and the like.

The hydrocolloid wound gel is applied to the wound generally from a tube to cleanse and debride wounds, absorb wound exudate and to enhance healing. Usually the wound cavity is partially filled with the gel and the wound sealed with an occlusive dressing. As exudate is generated, it is absorbed by the gel/dressing combination which swells to fill the entire wound cavity. Usually, the hydrocolloid wound gel will not be required to be replaced for several days.

Thus it is apparent from the foregoing description that the objects of this invention have been attained. A novel hydrocolloid wound gel has been invented which has some exudate absorbing capacity, debridement activity and promotes wound healing. In addition, a novel method of treating wounds has been invented.

While this invention has been described and exemplified in terms of its preferred embodiment, those skilled in the art will appreciate that modifications can be made without departing from the spirit and scope of this invention.

We claim:

1. A hydrocolloid wound gel composition which comprises:

(a) from about 0.05% to 1.0% by weight of a pectin;

(b) from about 2.0% to 4.5% by weight of sodium carboxymethylcellulose;

(c) from about 15.0% to 20.0% by weight of propylene glycol; and (d) water in a sufficient amount to make up the difference between the amount of ingredients (a)–(c) and 100% by weight.

2. The hydrocolloid wound gel of claim 1 wherein said wound gel composition comprises:

(a) about 3.4% by weight of sodium carboxymethylcellulose;

(b) about 0.1% by weight of pectin;

(c) about 15.0% by weight of propylene glycol; and (d) about 81.5% by weight of purified water.

3. The hydrocolloid wound gel of claim 1 wherein said wound gel composition contains a pharmacologically active ingredient.

4. A method of treating a wound, which comprises applying a hydrocolloid wound gel composition to said wound, wherein said hydrocolloid wound gel composition comprises:

(a) from about 0.05% to 1.0% by weight of pectin;

(b) from about 2.0% to 4.5% by weight of sodium carboxymethylcellulose (c) from about 15.0% to 20.0% by weight of propylene glycol; and (d) water in an amount to make up the difference between the amount of ingredients (a)–(c) and 100% by weight.

5. The method of treating a wound of claim 4 wherein the hydrocolloid wound gel composition comprises:

(a) about 0.1% by weight of pectin;

(b) about 3.4% by weight of sodium carboxymethylcellulose;

(c) about 15% by weight of propylene glycol; and (d) about 81.5% by weight of deionized water.

6. The method of treating a wound of claim 4 wherein the hydrocolloid wound gel composition contains a pharmaceutically active ingredient.

* * * * *